(12) United States Patent
Kohnle

(10) Patent No.: US 8,746,238 B2
(45) Date of Patent: Jun. 10, 2014

(54) INHALER

(75) Inventor: Joerg Kohnle, VS-Schwenningen (DE)

(73) Assignee: Aptar Radolfzell GmbH, Radolfzell (DE)

( * ) Notice: Subject to any disclaimer, the term of this patent is extended or adjusted under 35 U.S.C. 154(b) by 378 days.

(21) Appl. No.: 13/134,611

(22) Filed: Jun. 10, 2011

(65) Prior Publication Data

US 2011/0303221 A1 Dec. 15, 2011

(30) Foreign Application Priority Data

Jun. 15, 2010 (DE) .......................... 10 2010 024 912

(51) Int. Cl.
*A61M 15/00* (2006.01)

(52) U.S. Cl.
USPC ................ 128/200.23; 128/200.14; 222/23; 222/160; 222/162

(58) Field of Classification Search
None
See application file for complete search history.

(56) References Cited

U.S. PATENT DOCUMENTS

| | | | | |
|---|---|---|---|---|
| 3,814,297 A | * | 6/1974 | Warren | 222/402.13 |
| 4,509,515 A | * | 4/1985 | Altounyan et al. | 128/200.23 |
| 5,184,761 A | * | 2/1993 | Lee | 222/402.2 |
| 5,422,314 A | | 6/1995 | Sekiba | |
| 5,544,647 A | * | 8/1996 | Jewett et al. | 128/200.23 |
| 5,587,606 A | | 12/1996 | Sekiba | |
| 5,676,129 A | | 10/1997 | Rocci, Jr. et al. | |
| 5,724,986 A | * | 3/1998 | Jones et al. | 600/538 |
| 5,758,638 A | * | 6/1998 | Kreamer | 128/200.23 |
| 5,954,047 A | * | 9/1999 | Armer et al. | 128/200.23 |
| 6,029,659 A | * | 2/2000 | O'Connor | 128/203.12 |
| 6,119,684 A | | 9/2000 | Noehl et al. | |
| 6,138,669 A | | 10/2000 | Rocci, Jr. et al. | |
| 6,341,603 B1 | * | 1/2002 | Howlett | 128/200.23 |
| 6,390,088 B1 | | 5/2002 | Noehl et al. | |
| 2005/0028815 A1 | | 2/2005 | Deaton et al. | |
| 2009/0151723 A1 | | 6/2009 | Lang et al. | |
| 2009/0308385 A1 | * | 12/2009 | Brewer et al. | 128/203.12 |

FOREIGN PATENT DOCUMENTS

| | | |
|---|---|---|
| WO | WO 91/06334 A1 | 5/1991 |
| WO | WO 92/17231 | 10/1992 |
| WO | WO 96/00595 A1 | 1/1996 |
| WO | WO 97/33640 A1 | 9/1997 |
| WO | WO 2005/009325 A2 | 2/2005 |
| WO | WO 2008/006527 A1 | 1/2008 |

* cited by examiner

*Primary Examiner* — Tan-Uyen T Ho
*Assistant Examiner* — Eric Bryant
(74) *Attorney, Agent, or Firm* — Flynn, Thiel, Boutell & Tanis, P.C.

(57) ABSTRACT

An inhaler for the oral administration of a pharmaceutical medium, having a housing with a mouthpiece, a container unit accommodated in an inhalation region of the housing and including a medium container and an outlet connector having an outlet orifice, which outlet connector is capable of being moved relative to the medium container for the purpose of triggering a discharging operation, and a discharge sensor for the detection of a discharging operation.

The housing has a main portion and a detecting wall portion capable of movement relative to the main portion and which is configured and/or disposed for displacement relative to the main portion during a discharging operation, and the discharge sensor detects the displacement of the detecting wall portion in relation to the main portion of the housing.

19 Claims, 1 Drawing Sheet

US 8,746,238 B2

INHALER

FIELD OF APPLICATION AND PRIOR ART

This application claims the priority of the German patent application No. 10 2010 024 912.2. The whole disclosure of this prior application is herewith incorporated by reference into this application.

The invention relates to an inhaler for the oral administration of a pharmaceutical medium. A generic inhaler of such type includes a housing including a mouthpiece, a container unit, which is accommodated in an inhalation region of the housing and which comprises a medium container and an outlet connector having an outlet orifice, which connector is capable of being displaced relatively to the medium container for the purpose of carrying out a discharging operation, and further including a discharge sensor for detecting the discharge of medium.

Generic inhalers are usually referred to as an MDI (Metered-Dose Inhaler) and a pMDI (pressurized Metered-Dose Inhaler). Such inhalers are used for administering medicines that are intended to pass in an atomized form into the lungs of the user for the purpose of treating respiratory disorders. The inhalers include the aforementioned housing including the aforementioned container unit inserted therein. The housing has an air intake that allows air to be drawn in through the inhalation region of the housing toward the mouthpiece. At the same time that air is drawn in, medium is discharged from the medium container by displacing the medium container relatively to the outlet connector so that the air drawn in mixes with the atomized medium and is inhaled so as to pass into the lungs.

Medium is discharged from the medium container by displacing the medium container relatively to the outlet connector. In the simplest case, the medium container in generic inhalers can protrude to a certain extent from the air intake of the housing for this purpose, so that it can be subjected to direct manual force in order to be displaced relatively to the outlet connector inserted in a mating recess in the housing.

Generic inhalers are provided with a discharge sensor for detecting the discharging operation, more particularly for the purpose of counting the discharging operations. This enables a user to know the number of doses of medium still remaining in the medium container and thus to estimate how long the medium in the medium container will last.

Various ways of designing the discharge sensor are known in the prior art.

WO 1997/033640 A1 describes a pressure sensor that is disposed in a channel provided for discharging the medium and that makes it possible to detect the discharge of medium. This design is comparatively complex and expensive.

WO 1991/0006334 A1 discloses a design in which the discharging operation is detected mechanically by sensing the movement of the medium container in the inhalation region of the housing. A solution comparable thereto is disclosed in WO 1996/000595 A1. WO 2005/009325 A2 also describes a number of embodiments, most of which provide a push-button that is disposed in the inhalation region of the housing and is activated during displacement of the medium container in the inhalation region. Furthermore, this document also discloses that a push-button can be provided on the external surface of the housing, which push-button is inevitably actuated manually when force is applied manually to the medium container to move it relatively to the housing.

The disadvantage of the embodiments having a push-button that directly detects the movement of the medium container in the inhalation region is that they frequently do not ensure reliable detection of the discharge of medium, since the position of the container unit in the interior of the housing is subject to tolerances that makes it possible for the medium container to move past the switch. The resulting failure to detect a discharging operation is basically regarded as being more critical than an erroneous detection of a discharging operation that has actually not taken place. Furthermore, there is the risk of the push-button malfunctioning as a result of exposure to moisture, since it is disposed directly in the inhalation region, and as a result, the discharging operations will not be detected reliably.

SUMMARY OF THE INVENTION

It is an object of the invention to develop a generic inhaler to the effect that it can reliably detect discharging operations. It is a further aim to achieve a cost-effective design for the inhaler.

According to the invention, this object is achieved in that the housing includes a main portion and a detecting wall portion, which is displaceable relatively to the main portion and is configured and/or disposed such that it is displaced relatively to the main portion of the housing during a discharging operation. Furthermore, the discharge sensor is configured to detect the displacement of the detecting wall portion relatively to the main portion of the housing.

Thus there is provided, according to the invention, a wall portion that delimits the inhalation region and isolates the same from, in particular, the environment or a chamber for accommodating electronic components, and also a detecting wall portion that is capable of being moved relatively to a main portion of the housing and that moves when the medium container is displaced within the inhalation region. This movement of the detecting wall portion is detected by the discharge sensor, which does not directly detect the movement of the medium container.

An inhaler of the invention has the features of the generic inhalers described above, and thus preferably includes an electronic system configured to evaluate the signals of the discharge sensor, which is preferably in the form of a push-button. Preferably, this electronic system includes an integrated circuit used particularly for counting the discharging operations, and preferably includes a battery as an energy-storage device and an output unit in the form of a display that reveals the number of doses that have already been discharged or are still present in the medium container.

The main portion of the housing, in relation to which the detecting wall portion can be moved, includes those portions of the external surface of the housing that are to be held by the user in accordance with the designated use of the inhaler. These portions of the external surface of the housing include a cylindrical housing portion, which surrounds the container unit, and all components of the housing, such as the mouthpiece, that are immovable relatively thereto. The detecting wall portion is movable relatively to this main portion, and is connected to the main portion in such a way that the detecting wall portion returns to its starting position on completion of a discharging operation without any need for the application of manual force to the medium container. The detecting wall portion, which is in the form of a portion of the housing, is preferably made of the same material as the main portion, more particularly of plastics material. Preferably, the detecting wall portion is connected integrally to at least those parts of the main portion of the housing that surround the detecting wall portion, wherein a connecting region between the main portion and the detecting wall portion is of a deformable nature. This integral connection of the detecting wall portion to parts of the main portion simplifies the manufacture of the inhaler, since the detecting wall portion can be provided directly during the manufacture of the housing. Furthermore, this integral connection provides a simple way of achieving the aforementioned automatic return of the detecting wall portion to its initial position by the use of an appropriate resilient construction of the connecting region. Furthermore, the integral connection is also of advantage with respect to achieving the desired liquid-tightness. For this purpose, provision is further made for the connecting region to surround the detecting wall portion around its periphery and thus connect the detecting wall portion in a liquid-tight manner to the main portion of the housing. In such a case, the connecting region is preferably in the form of a region having a wall thickness that is significantly less than that of the detecting wall portion and the main portion. The connecting region can have a series of concertina folds in order to ensure ease of deformation. Apart from the liquid-tight construction having the circumferential connecting region described above, it is also possible to establish connection of the detecting wall portion to the main portion of the housing by means of discrete and, in particular, thin-walled bridges of material.

Preferably, the discharge sensor is provided on that side of the detecting wall portion that is remote from the inhalation region. The discharge sensor is thus disposed in a protected zone. There is therefore no risk of damage being imparted to the discharge sensor during insertion of the container unit. In particular, the liquid-tight construction of the connecting region described above also ensures that the discharge sensor that is remote from the inhalation region is not detrimentally influenced by liquid present in the inhalation region.

The detecting wall portion can cooperate with the container unit in such a way that the container unit slides along the detecting wall portion in the course of its movement or the movement of its medium container and deflects the detecting wall portion relatively to the main portion of the housing, this deflection being detected by the discharge sensor. However, one embodiment is considered advantageous in which the detecting wall portion is immovable with respect to the medium container of the container unit or the outlet connector of the container unit. In such an embodiment, the insertion of the container unit into the housing results in a state in which any one of the two components of the container unit, which are movable relatively to each other, stays immovable with respect to the detecting wall portion. This ensures very sure cooperation between the detecting wall portion and that component of the container unit that is immovable in relation thereto. The immovability of the component of the container unit with respect to the detecting wall portion can be achieved by means of a non-positive or positive connection between the outlet connector and the detecting wall portion. A simple plug-and-socket connection may be sufficient for this purpose.

It is very preferable for the detecting wall portion to stay immovable with respect to the outlet connector of the container unit during operation. It is particularly preferable for this purpose when the detecting wall portion includes a recess for the accommodation of the outlet connector and preferably a discharge nozzle that is connected to the said recess via a channel. This discharge nozzle opens into the inhalation region of the housing and defines the region in which the medium coming from the medium container mixes with the air drawn in by the user during inhalation. In such an embodiment in which the detecting wall portion stays immovable with respect to the outlet connector, the detecting wall portion is disposed below the container unit in the conventional orientation of an MDI during use. When the medium container is pushed down relatively to the main portion of the housing, the detecting wall portion is accordingly displaced in the same direction, but to a lesser extent, relatively to the main portion of the housing. Such an embodiment has proved to be particularly reliable, since it prevents situations in which doses are erroneously counted due to tolerances in terms of the position of the container unit in the housing, for example, or situations in which an actuation that has in fact taken place is not counted or an actuation commenced but prematurely terminated before liquid has been discharged is counted.

Preferably, the discharge sensor, the detecting wall portion, and the container unit are adapted to each other and disposed in such a way that during displacement of the container unit relatively to the main portion of the housing, the detecting wall portion actuates the discharge sensor as soon as, or before, the operation of discharging medium from the medium container commences.

This means that the force required for causing deflection of the detecting wall portion to an extent which is sufficient to activate the discharge sensor by means of the detecting wall portion, is equal to, or less than, the force required to displace the outlet connector of the container unit relatively to the medium container to such an extent that the discharging operation commences. In the case of the aforementioned embodiment in which the detecting wall portion, which can be resiliently deflected in relation to the housing, always stays immovable with respect to the outlet connector during operation, the distance through which the medium container is displaced relatively to the main portion of the housing is divided into a sub distance through which the medium container is displaced relatively to the outlet connector and the detecting wall portion, and a sub distance through which the outlet connector and the detecting wall portion are displaced relatively to the main portion of the housing. The aforementioned behavior can be achieved by appropriately adapting the manner in which the detecting wall portion is connected to the main portion to the force required for displacing the outlet connector relatively to the medium container.

This type of adaptation ensures that an incomplete discharging operation resulting, for example, from insufficient displacement of the medium container relatively to the main portion of the housing is also registered by the discharge sensor and is allowed for when the discharging operations are counted. A deviation of the remaining amount of medium in the medium container, as determined by means of the counting process, from the actual amount of medium present is thus only possible in this way when the amount of medium still present in the medium container is underestimated. This prevents situations in which medium is presumed to be remaining in the medium container when there is in fact no more medium present.

The discharge sensor, preferably in the form of a push-button, can be provided, in particular, on the main portion of the housing and can be disposed in such a way that a surface of the push-button that can be displaced relatively to the base of the push-button is pressed down by the detecting wall portion during actuation of the inhaler. As mentioned above, the discharge sensor is preferably disposed on the side of the detecting wall portion that is remote from the inhalation region. It is particularly advantageous when the housing comprises two sub housings that can be coupled to each other by means of a coupling device, a first sub housing surrounding the inhalation region and comprising the detecting wall portion, whilst a second sub housing comprises the discharge sensor.

In such an embodiment, the first sub housing can be intended for disposal together with the container unit following usage thereof, whilst the second sub housing including the discharge sensor and preferably all other electronic components of the inhaler will be reused. In such a case, the discharge sensor is disposed in the second sub housing in such a way that an application of external force can activate the sensor, this application of force being carried out by means of the appropriately configured detecting wall portion in the coupled state of the sub housing.

In a development of this embodiment including two sub housings, the second sub housing has a sensor that is adapted to detect the coupled state of the two sub housings. This can be a separate sensor. The discharge sensor can also be configured so as to be able to detect firstly the coupled state and secondly the displacement of the detecting wall portion, for example as indicated by deflection of the push-button surface.

Preferably, the electronic components, more particularly the circuit provided for counting purposes, are configured in such a way that an actuation of the sensor provided for counting purposes is used for counting the doses only if the sub housings are in the coupled state.

In such an embodiment including two sub housings, very preferably the second sub housing has an interior region that is delimited in the region of the discharge sensor by a deformable or displaceable wall portion. This allows the electronic system to be fully encapsulated. In such a case and even in the decoupled state of the sub housings, the discharge sensor is not located without protection on the external surface of the second sub housing. Instead, it is protected by this wall portion, which can be in the form of a thin-walled membrane, for example.

BRIEF DESCRIPTION OF THE DRAWINGS

Additional aspects and advantages of the invention are revealed in the claims and the following description of a preferred exemplary embodiment of the invention which is explained below with reference to the figures, in which:

DETAILED DESCRIPTION

Figure 1:
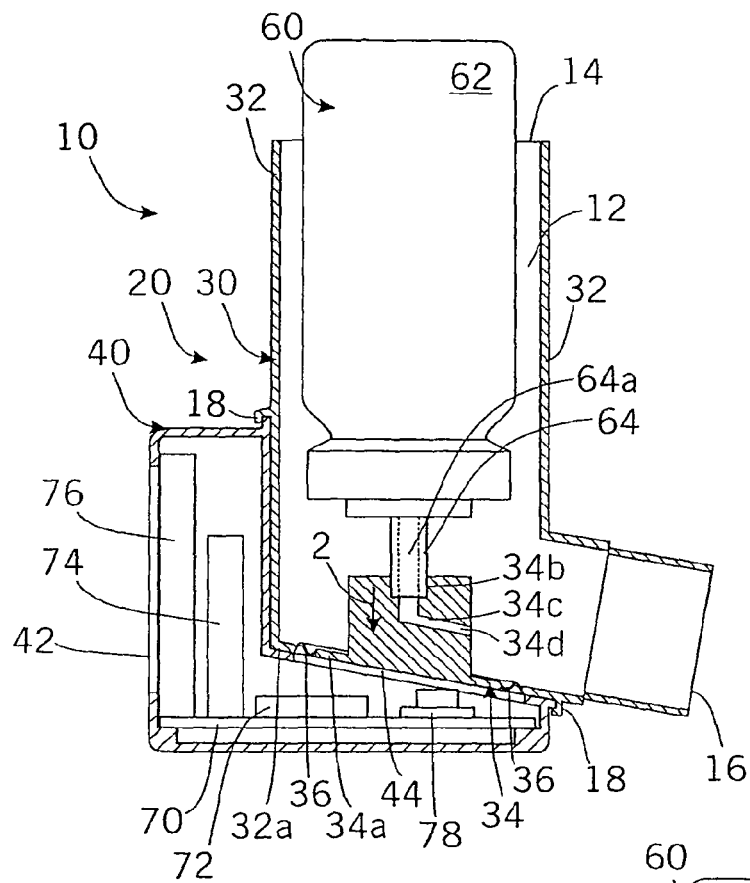
FIG. 1 shows an inhaler of the invention prior to actuation thereof.

FIG. 1 shows an inhaler 10 of the invention prior to actuation thereof.

The inhaler 10 includes a housing 20 that is composed of two sub housings 30, 40 that can be joined and separated by means of a coupling device 18 without the use of tools.

The first sub housing 30 has approximately the shape of a conventional MDI. Sub housing 30 surrounds an approximately L-shaped inhalation region 12, the top end of which is open to form an air intake 14 and the bottom end of which is likewise open to form a mouthpiece 16. The external walls 32, 34 of this first sub housing 30 are, with the exception of a detecting wall portion 34, immovable with respect to each other and to the walls of the second sub housing 40 during inhalation and form the main portion 32 of the sub housing 30. Only the aforementioned detecting wall portion 34 provided at the bottom end of the first sub housing 30 is movable relatively to this main portion 32 of the first sub housing 30. This movability is achieved in that the detecting wall portion 34 is integrally connected to the main portion 32 by means of a peripheral, thin-walled connecting region 36 that is shaped as a series of concertina folds. This permits relative displacement of the detecting wall portion 34 in the direction of the arrow 2.

The detecting wall portion 34 includes a flat marginal area 34a that aligns with the surrounding bottom portions 32a of the main portion 32, to which it is integrally connected. The detecting wall portion 34 is configured to be thicker at the center, and in this thick region there are provided a cylindrical accommodation recess 34b and a channel 34c extending therefrom to form a nozzle orifice 34d.

A container unit 60 is inserted in the inhalation region 12 of the first sub housing 30. This container unit has a medium container 62 and an outlet connector 64 including an outlet orifice 64a. For the purpose of discharging a medium from the medium container 62, the outlet connector can be displaced relatively to the medium container 62 against a counteracting force. In the state shown in FIG. 1, in which the container unit has already been inserted into the first sub housing 30, the outlet connector 64 is positioned in the accommodating recess 34b in the detecting wall portion 34. The outlet connector 64 and the accommodating recess 34b can be adapted to each other in such a way that they form a non-positive clamping connection. The top end of the medium container 62 protrudes from the first sub housing 30 through the air intake 14, and the protruding portion thereof is intended for actuation of the inhaler 10.

The second sub housing 40 includes all electronic components of the inhaler 10, these components being represented merely diagrammatically in the figures. The electronic components include a main board 70, on which an integrated circuit 72, an energy-storage device in the form of a battery 74, and an LCD display 76 are provided. The LCD display 76 is positioned in such a way that it can be read through an opening 42 in the wall of the second sub housing 40. The second sub housing 40 includes an opening 44 in the region of the detecting wall portion 34. A push-button or control switch 78 is disposed on the main board 70 below this opening 44.

The aforementioned electronic components 70, 72, 74, 76 are configured to detect and count the actuations of the push-button 78, the resulting actuation-count being indicated on the display 76. Thus the electronic components jointly serve to count the discharging operations that have taken place.

Figure 2:
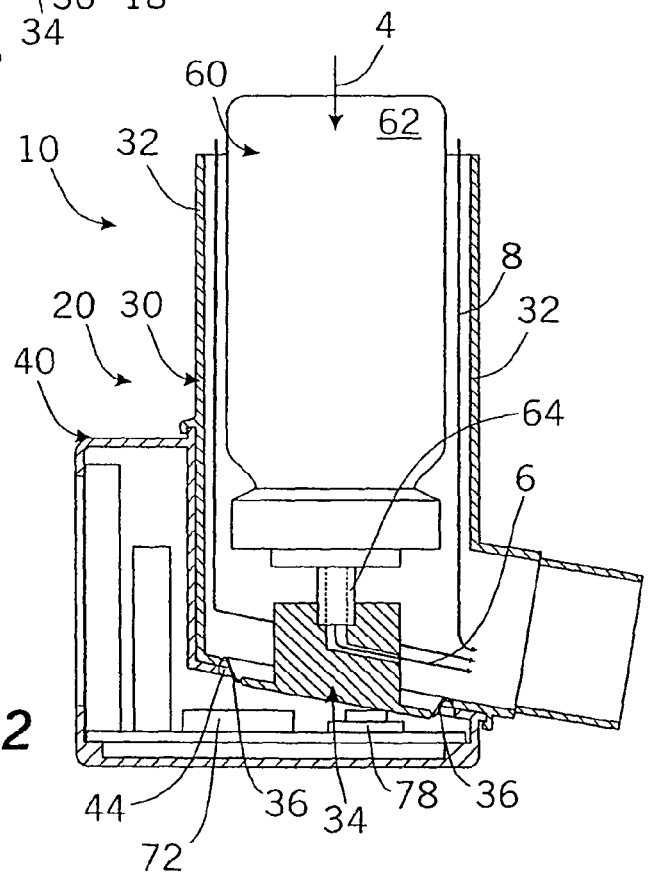
FIG. 2 shows the inhaler of the invention during actuation thereof.

The mode of operation of the inhaler is as follows: For the purpose of operating the inhaler as intended, the mouthpiece 16 is enclosed by the lips of the user, who then draws in air. At the same time, the medium container 62 is pushed down manually relatively to the main portion 32 of the first sub housing 30 in the direction of the arrow 4. As shown in FIG. 2, this results firstly in the outlet connector 64 being pushed in relatively to the medium container 62. Furthermore, a simultaneous resilient deflection of the connecting region 36 also causes the detecting wall portion 34 pertaining to the first sub housing 30 to be pushed down. In doing so, the detecting wall portion 34 enters the second sub housing 40 through the opening 44 therein and comes into contact with the push-button 78. Continued displacement of the medium container 62 causes an acknowledgement signal to be sent at approximately the same time by the push-button 78 to the integrated circuit 72 and the operation of discharging the medium commences, in the course of which medium passes from the medium container 62 in the direction of the arrow 6 into the inhalation region 12, where it mixes with the air drawn in by the user in the direction of the arrows 8, the mixture being sucked in by the user through the mouthpiece 16.

As described above, the discharging operation is detected by the integrated circuit 72 due to the actuation of the control switch 78 and is indicated on the LCD display 76. The number of doses shown on the LCD display 76 may relate to the doses still remaining in the container or to the doses that have already been administered.

Once all of the doses in the medium container 62 have been consumed, the sub housings 30, 40 can be decoupled from each other, and a new first sub housing 30 comprising a new container unit 60 can be coupled to the reusable second sub housing 40 including the electronic components 70, 72, 74, 76, 78.

In a development of the invention (not shown), the opening 44 pertaining to the second sub housing 40 can also be closed by a membrane or a wall portion of similar construction as the detecting wall portion 34a such that the separated second sub housing 40 is hermetically sealed from the environment.

The invention claimed is:

1. An inhaler for oral administration of a pharmaceutical medium, comprising:
    a housing having a mouthpiece;
    a container unit accommodated in an inhalation region of said housing and including:
        a medium container disposed for movement relative to said housing; and
        an outlet connector having an outlet orifice, said outlet connector being movable relative to said medium container for triggering a discharging operation; and
    a discharge sensor disposed to detect the discharging operation;
    wherein:
    said housing has a main portion and a detecting wall portion movable relative to said main portion and configured and/or disposed wherein said detecting wall portion is displaced relative to said main portion during the discharging operation, said detecting wall portion being formed integrally with said main portion of said housing and a connecting region between said main portion and said detecting wall portion is deformable, said detecting wall portion including therein an accommodation recess in which said outlet connector is disposed; and
    said discharge sensor is adapted to detect the displacement of the detecting wall portion in relation to said main portion of said housing.

2. The inhaler for oral administration of a pharmaceutical medium as defined in claim 1, wherein said connecting region surrounds said detecting wall portion around a periphery thereof and connects said detecting wall portion to said main portion of said housing in a liquid-tight manner.

3. The inhaler for oral administration of a pharmaceutical medium as defined in claim 1, wherein said discharge sensor is provided on a side of said detecting wall portion remote from said inhalation region.

4. The inhaler for oral administration of a pharmaceutical medium as defined in claim 1, wherein said detecting wall portion and said medium container or said outlet connector, are immovable with respect to each other.

5. The inhaler for oral administration of a pharmaceutical medium as defined in claim 1, wherein said detecting wall portion includes a discharged nozzle connected to said accommodation recess via a channel defined in said detecting wall portion, said accommodation recess communicating with said outlet orifice and said outlet orifice communicating with said medium container.

6. The inhaler for oral administration of a pharmaceutical medium as defined in claim 1, wherein said discharge sensor, said detecting wall portion and said container unit are adapted to each other and disposed such that when there is a displacement of said container unit relative to said main portion of said housing, said detecting wall portion actuates said discharge sensor as soon as, or before, the discharging operation commences.

7. The inhaler for oral administration of a pharmaceutical medium as defined in claim 1, wherein said housing has two sub housings coupled together by a coupling device and wherein:
    a first sub housing of said housing surrounds said inhalation region and comprises said detecting wall portion; and
    a second sub-housing of said housing comprises said discharge sensor.

8. The inhaler for oral administration of a pharmaceutical medium as defined in claim 7, wherein said second sub housing has an interior region which is delimited adjacent said discharge sensor by a deformable or movable wall portion.

9. The inhaler for oral administration of a pharmaceutical medium as defined in claim 1, wherein said detecting wall portion is operatively connected to said medium container for movement therewith during the discharging operation.

10. The inhaler for oral administration of a pharmaceutical medium as defined in claim 9, wherein said outlet connector interconnects said medium container and said detecting wall portion for movement with one another during the discharging operation.

11. The inhaler for oral administration of a pharmaceutical medium as defined in claim 1, wherein said medium container has an actuating portion disposed for manual manipulation by a user to effect the discharging operation by movement of said medium container relative to said housing.

12. The inhaler for oral administration of a pharmaceutical medium as defined in claim 11, wherein said outlet connector interconnects said medium container and said detecting wall portion for movement with one another upon manual manipulation of said actuating portion of said medium container.

13. The inhaler for oral administration of a pharmaceutical medium as defined in claim 1, wherein said housing includes a first housing member including said main portion, said detecting wall portion and said mouthpiece, said main portion, said detecting wall portion and said mouthpiece together defining said inhalation region, said housing further including a second housing member connected to said first housing member and disposed adjacent said detecting wall portion, said second housing member defining an interior which is sealed from pharmaceutical medium within said inhalation region of said first housing member, said discharge sensor being disposed within said interior of said second housing member and said detecting wall portion is disposed to displace in a direction towards said discharge sensor during the discharging operation.

14. An inhaler for oral administration of a pharmaceutical medium, comprising:
    a housing including a main housing portion defining an inhalation region therein, a detecting wall portion connected to said main housing portion for movement relative to said main housing portion, and a mouthpiece;
    a container unit disposed in said inhalation region of said main housing portion, said container unit including a medium container and an outlet connector having an outlet orifice in communication with pharmaceutical medium within said medium container, said medium container including an actuating portion configured for manual manipulation by a user to effect a discharging operation by movement of said medium container relative to said housing, said detecting wall portion being operatively connected to said medium container for movement therewith, said detecting wall portion being disposed to move said outlet connector relative to said medium container upon manual manipulation of said actuating portion and movement of said medium container relative to said main housing portion to cause discharge of the pharmaceutical medium from said medium container through said mouthpiece; and a discharge sensor disposed to detect movement of said detecting wall portion relative to said main housing portion.

15. The inhaler for oral administration of a pharmaceutical medium as defined in claim 14, wherein said detecting wall portion is formed integrally with said main housing portion, said detecting wall portion having a periphery connected to said main housing portion by a deformable connecting region, said connecting region surrounding said periphery and connecting said detecting wall portion to said main housing portion in a liquid-tight manner.

16. The inhaler for oral administration of a pharmaceutical medium as defined in claim 14, wherein said housing includes a first housing member including said main housing portion, said detecting wall portion and said mouthpiece, said main housing portion, said detecting wall portion and said mouthpiece together defining said inhalation region, said housing further including a second housing member connected to said first housing member and disposed adjacent said detecting wall portion, said second housing member defining an interior which is sealed from the pharmaceutical medium within said inhalation region of said first housing member, said discharge sensor being disposed within said interior of said second housing member.

17. The inhaler for oral administration of a pharmaceutical medium as defined in claim 14, wherein said detecting wall portion and said outlet connector are non-movably connected to one another.

18. The inhaler for oral administration of a pharmaceutical medium as defined in claim 14, wherein said outlet connector interconnects said medium container and said detecting wall portion for movement with one another.

19. The inhaler for oral administration of a pharmaceutical medium as defined in claim 18, wherein said detecting wall portion defines therein a recess in which said outlet connector is disposed and a channel in communication with both said recess and said outlet orifice of said outlet connector, said channel including a discharge nozzle disposed to discharge the pharmaceutical medium through said mouthpiece during the discharging operation.

* * * * *